United States Patent
Longepied

(10) Patent No.: US 9,247,972 B2
(45) Date of Patent: Feb. 2, 2016

(54) CUSTOMIZED OSTEOSYNTHESIS ASSEMBLY

(71) Applicant: OBL, Chatillon (FR)

(72) Inventor: Patrice Longepied, Sceaux (FR)

(73) Assignee: OBL, Chatillon (FR)

( * ) Notice: Subject to any disclaimer, the term of this patent is extended or adjusted under 35 U.S.C. 154(b) by 0 days.

(21) Appl. No.: 14/313,139

(22) Filed: Jun. 24, 2014

(65) Prior Publication Data

US 2014/0309638 A1   Oct. 16, 2014

Related U.S. Application Data

(63) Continuation of application No. 13/201,666, filed as application No. PCT/FR2010/000134 on Feb. 17, 2010, now Pat. No. 8,784,456.

(30) Foreign Application Priority Data

Feb. 17, 2009  (FR) ...................................... 09 00722

(51) Int. Cl.
*A61B 17/80* (2006.01)
*A61B 17/00* (2006.01)
*A61B 19/00* (2006.01)

(52) U.S. Cl.
CPC ......... *A61B 17/8071* (2013.01); *A61B 17/8085* (2013.01); *A61B 2017/00792* (2013.01); *A61B 2019/306* (2013.01); *Y10T 29/49799* (2015.01)

(58) Field of Classification Search
CPC ............. A61B 17/80–17/8076; A61B 17/8085
USPC .......... 606/70, 71, 280–299, 902–906; 433/7, 433/18, 19, 20, 23
See application file for complete search history.

(56) References Cited

U.S. PATENT DOCUMENTS 4,573,458 A * 3/1986 Lower ........................... 606/280
4,905,679 A * 3/1990 Morgan .......................... 606/70

(Continued)

FOREIGN PATENT DOCUMENTS

EP   1468656 A1   10/2004
FR   2531855 A1    2/1984

(Continued)

OTHER PUBLICATIONS

International Search Report dated Apr. 29, 2010 for related application PCT/FR2010/000134 filed Feb. 17, 2010 and published as WO2010-094857 on Aug. 26, 2010.

(Continued)

*Primary Examiner* — Christian Sevilla
*Assistant Examiner* — Eric S. Gibson
(74) *Attorney, Agent, or Firm* — EIP US LLP

(57) ABSTRACT

Disclosed embodiments relate to a customized assembly of osteosynthesis plates. The customized assembly of osteosynthesis plates is custom-made, for example I-shaped and/or L-shaped and/or cross-shaped and/or crow's-foot-shaped ones which are themselves customized according to the operation to be carried out and the future anatomy of the patient, characterized in that the osteosynthesis plates are connected together by a rod, the rod further comprising two protrusions (4) protruding from the rod towards the nasal orifice (8) of the patient into positions that correspond to the two ends (5, 6) of the base (7) of the nasal orifice (8) of the patient. The invention can be used during dental occlusion operations, for example.

14 Claims, 3 Drawing Sheets

(56) References Cited

U.S. PATENT DOCUMENTS

| | | | | |
|---|---|---|---|---|
| 5,413,577 | A * | 5/1995 | Pollock | 606/280 |
| 6,325,803 | B1 * | 12/2001 | Schumacher et al. | 606/71 |
| 6,423,068 | B1 * | 7/2002 | Reisberg et al. | 606/281 |
| 6,960,211 | B1 * | 11/2005 | Pfefferle et al. | 606/282 |
| 6,978,188 | B1 | 12/2005 | Christensen | 700/118 |
| 7,909,610 | B1 * | 3/2011 | Amato | 434/270 |
| 8,246,663 | B2 * | 8/2012 | Lovald et al. | 606/280 |
| 8,282,635 | B1 * | 10/2012 | Amato | 606/57 |
| 8,435,270 | B2 | 5/2013 | Furrer | |
| 8,784,456 | B2 * | 7/2014 | Longepied | 606/284 |
| 2002/0128654 | A1 * | 9/2002 | Steger et al. | 606/69 |
| 2002/0150856 | A1 | 10/2002 | Payton | |
| 2005/0065521 | A1 * | 3/2005 | Steger et al. | 606/69 |
| 2005/0130092 | A1 * | 6/2005 | Minoretti et al. | A61B 17/663 433/7 |
| 2006/0235397 | A1 * | 10/2006 | Sanders et al. | 606/69 |
| 2007/0238069 | A1 * | 10/2007 | Lovald et al. | 433/173 |
| 2008/0281327 | A1 * | 11/2008 | Helfteren | 606/71 |
| 2009/0061377 | A1 | 3/2009 | Cope | |
| 2011/0144698 | A1 * | 6/2011 | Buchbinder et al. | 606/280 |
| 2011/0269100 | A1 * | 11/2011 | Furrer et al. | 433/72 |
| 2011/0301609 | A1 * | 12/2011 | Longepied | 606/71 |
| 2012/0029574 | A1 * | 2/2012 | Furrer et al. | 606/280 |
| 2012/0277749 | A1 * | 11/2012 | Mootien et al. | 606/70 |
| 2014/0074438 | A1 | 3/2014 | Furrer | |

FOREIGN PATENT DOCUMENTS

| | | | |
|---|---|---|---|
| FR | 2626460 | A1 | 8/1989 |
| FR | 2725124 | A1 | 4/1996 |

OTHER PUBLICATIONS

International Preliminary Report on Patentability dated Aug. 23, 2011 for related application PCT/FR2010/000134 filed Feb. 17, 2010 and published as WO2010-094857 on Aug. 26, 2010.

* cited by examiner

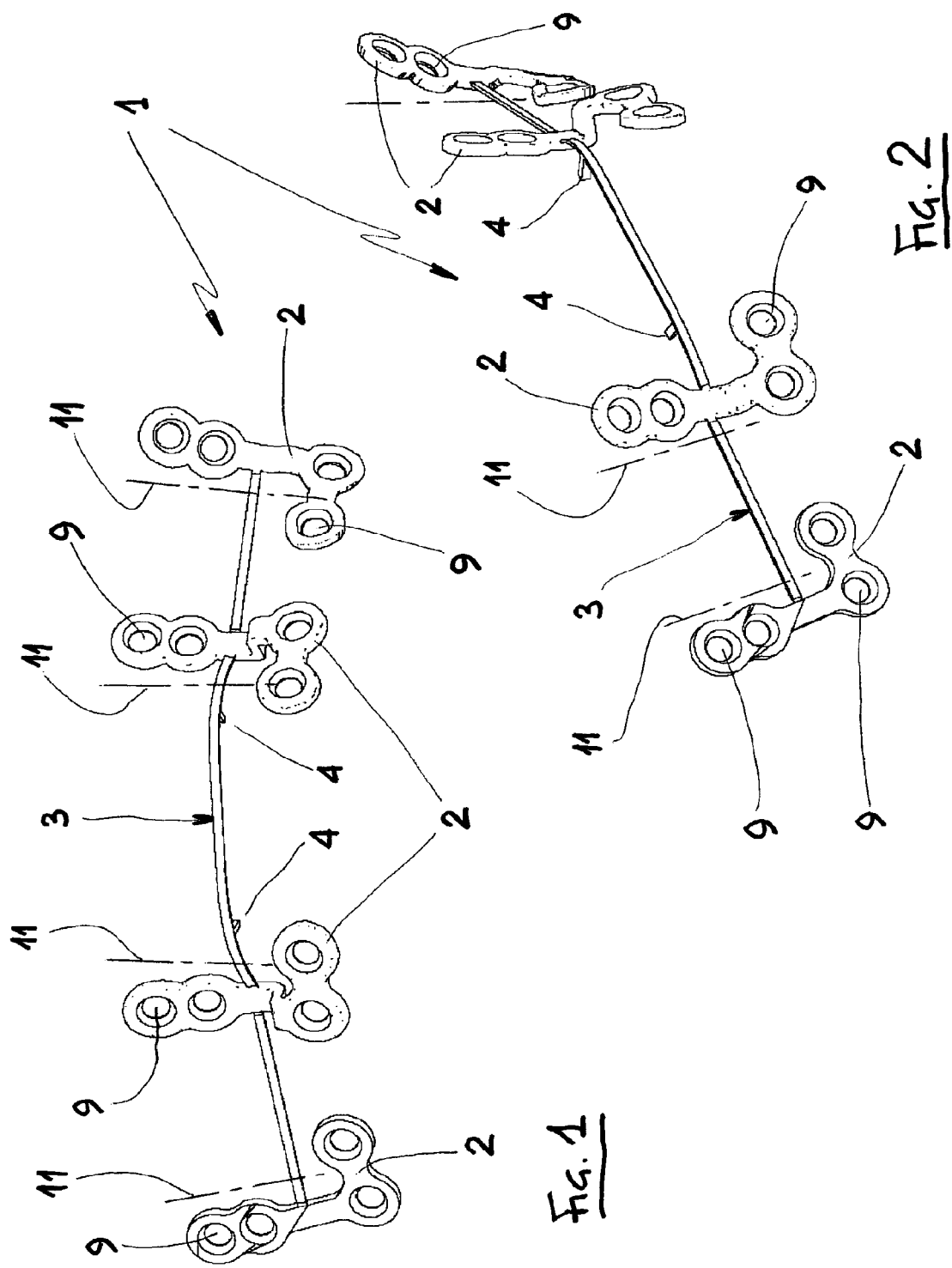

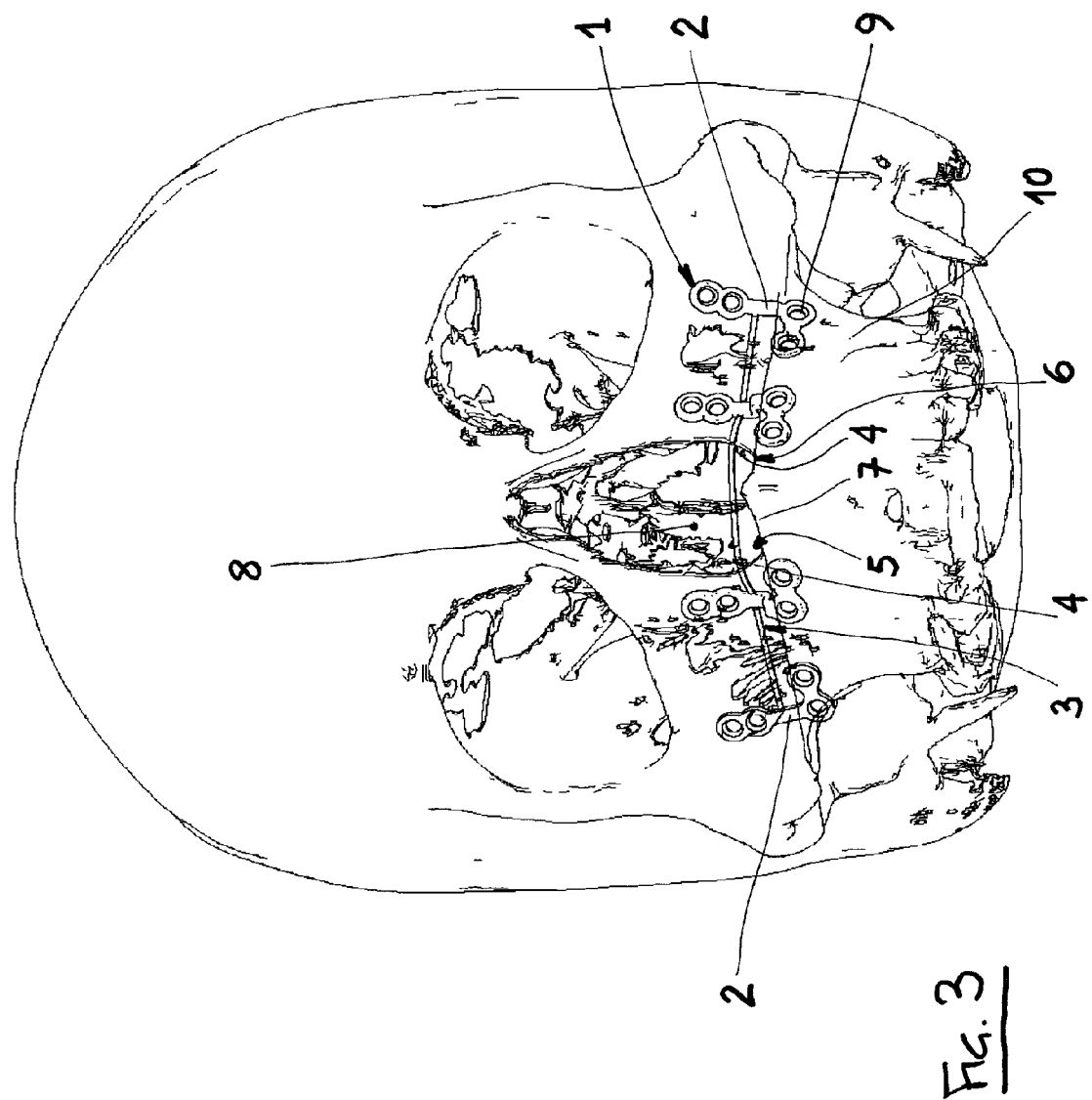

CUSTOMIZED OSTEOSYNTHESIS ASSEMBLY

CROSS-REFERENCE TO RELATED APPLICATIONS

This application is a continuation under 35 U.S.C. §120 of U.S. application Ser. No. 13/201,666, filed Aug. 16, 2011 (and published as U.S. Patent Pub. No. 2011/0301609 A1 on Dec. 8, 2011), which is a 35 U.S.C. 371 national stage entry of International Application No. PCT/FR2010/000134, filed Feb. 17, 2010 (and published by the International Bureau as International Publication No. WO2010/094857 on Aug. 26, 2010), which claims priority to French Patent Application No. 09.00722, filed Feb. 17, 2009. The entire contents of each of the above-referenced applications are hereby incorporated by reference.

BACKGROUND OF THE INVENTION

1. Field of the Invention

The present invention relates to a customized assembly of at least two osteosynthesis plates, for example straight I-shaped and/or L-shaped and/or cross-shaped and/or crow's-foot-shaped ones which are themselves customized according on the one hand to the operation to be carried out on one jaw or on both jaws of a patient and, on the other hand, according to the future anatomy of the patient.

It also relates to a method for implanting said customized assembly on the patient.

2. Description of the Related Technology

In the context of plastic surgery, in particular orthognatic and traumatic surgery or also during certain surgical interventions and notably during an osteosynthesis maxillo-mandibular intervention, it is known that the latter does not modify the occlusion or that it does not modify the occlusion relationships, whether it is total, i.e. by modifying an alveolar arch, or segmental, i.e. pertaining only to part of the ridge—it is always necessary to resort to setting osteosynthesis plates, i.e. fastening plates screwed between the bone parts that are then disjoined.

Such plates are well known, in particular from French patent published under No. 2,531,855 or also French patent published under No. 2,725,124.

These osteosynthesis plates, which are more and more often made of titanium, are bent by hand by the surgeon, with pincers, so that they adapt perfectly to the future anatomy of the patient.

It is also known how to make, on the basis of data from a scanner or an MRI, an osteosynthesis simulation thanks to which it is possible to electively move the maxillary and/or mandibular bone part forwards or backwards until the desired arrangement of the patient's teeth in relation to one another is achieved.

Before proceeding with such a dental occlusion operation, it is known how to simulate in advance the results of the operation on the patient and it is thus consequently possible to prepare customized osteosynthesis plates of various shapes that will have to be screwed at the appropriate places into the bone elements of one or both jaws of the patient, until the bone has healed up.

This preparation will itself lead, as has been stated by way of preliminaries, to all desired curvatures of the osteosynthesis plates, in order to adapt the latter perfectly to the future anatomy of the patient.

Having said this, and this problem having not been resolved yet, nothing will make it possible to guarantee that the surgeon will place exactly at the right place on the patient's jaw or jaws the osteosynthesis plates customized in advance.

SUMMARY

The aim of the present invention is to propose a solution to this problem by proposing a customized assembly of at least two osteosynthesis plates that are themselves customized.

Such an assembly structure is characterized in that the osteosynthesis plates are connected together by a rod, said rod further comprising two protrusions protruding from said rod towards the nasal orifice of the patient into positions that correspond to the two ends of the base of the nasal orifice of the patient.

As the position of the lower corners of the patient's nasal orifice cannot change their position, the fact that the surgeon uses them as natural references to lodge the protrusions of the inventive assembly structure and thus to place said assembly structure either on the lower jaw or on the upper jaw of the patient subjected to the operation, guarantees that all osteosynthesis plates of said structure will occupy without exception the locations that have been designed in advance to accommodate them.

Advantageously, the two protrusions each have the shape of a stud, of a finger, of a lug or of a spur.

As the two protruding reference points thus provided, by virtue of its construction, on the rod of the inventive assembly structure are protrusions that come to rest in the lower corners of the patient's nasal orifice, it is easier for the surgeon to place said assembly structure with the greatest precision possible.

The rod of the assembly structure according to the invention further advantageously also perfectly follows the anatomy of the patient.

In another preferred embodiment, the assembly structure according to the invention is characterized by the fact that, close to each of its plates, the rod of said structure has zones of reduced resistance designed to make it easier for the surgeon to cut all the connecting parts between the different osteosynthesis plates of said structure.

After the assembly structure according to the invention has been placed in the ideal position by the surgeon and then all the osteosynthesis plates have been fastened by screwing into the bone of the patient's upper or lower jaw, it is evidently desirable to immediately remove all the connecting parts between said plates, including the part that has the protrusions that have allowed the assembly structure to be placed precisely into the ideal position on the patient's jaw. The zones of reduced resistance provided in the immediate vicinity of the plates will just simplify the surgeon's task during the entire operation of removing those parts of the inventive assembly structure that have become superfluous.

The assembly structure according to the invention is advantageously made of a single piece and is preferably made of titanium.

The present invention also relates to a method for implanting at least two osteosynthesis plates on the maxillary and/or mandible of a patient during a dental occlusion operation, said method being characterized in that, as preliminary to said operation, the results of the operation on the patient are simulated in advance, the position and shape of the osteosynthesis plates are determined according to the future anatomy of the patient, an assembly of at least two osteosynthesis plates is custom-made, for example I-shaped and/or L-shaped and/or cross-shaped and/or crow's-foot-shaped ones, which are themselves customized according to the operation to be carried out and the future anatomy of the patient, said assembly comprising a rod that connects together the osteosynthesis plates and that further comprises two protrusions corresponding to the lower corners of the patient's nasal orifice, and further characterized in that, after the operation, the surgeon ideally implants said customized assembly by placing its two protrusions in the lower corners of the patient's nasal orifice, then fastens all the osteosynthesis plates by means of screws penetrating the bone elements of the upper or lower jaw in question, then cuts, close to each of the osteosynthesis plates of said assembly, all the connecting parts formed by the rod between said plates.

BRIEF DESCRIPTION OF THE DRAWINGS

The invention will be better understood by reading the following description and with reference to the attached drawings that illustrate in non-limiting manner an embodiment of said invention and in which:

FIGS. 1 and 2 represent, as seen from the front and the side respectively, an embodiment of the customized assembly structure of osteosynthesis plates according to the invention, said assembly structure comprising four L-shaped plates in this example.

FIG. 3 illustrates in a front view the placing, in an ideal position on the upper jaw of a patient, of the customized assembly of FIGS. 1 and 2.

DETAILED DESCRIPTION OF CERTAIN INVENTIVE EMBODIMENTS

Figure 4:
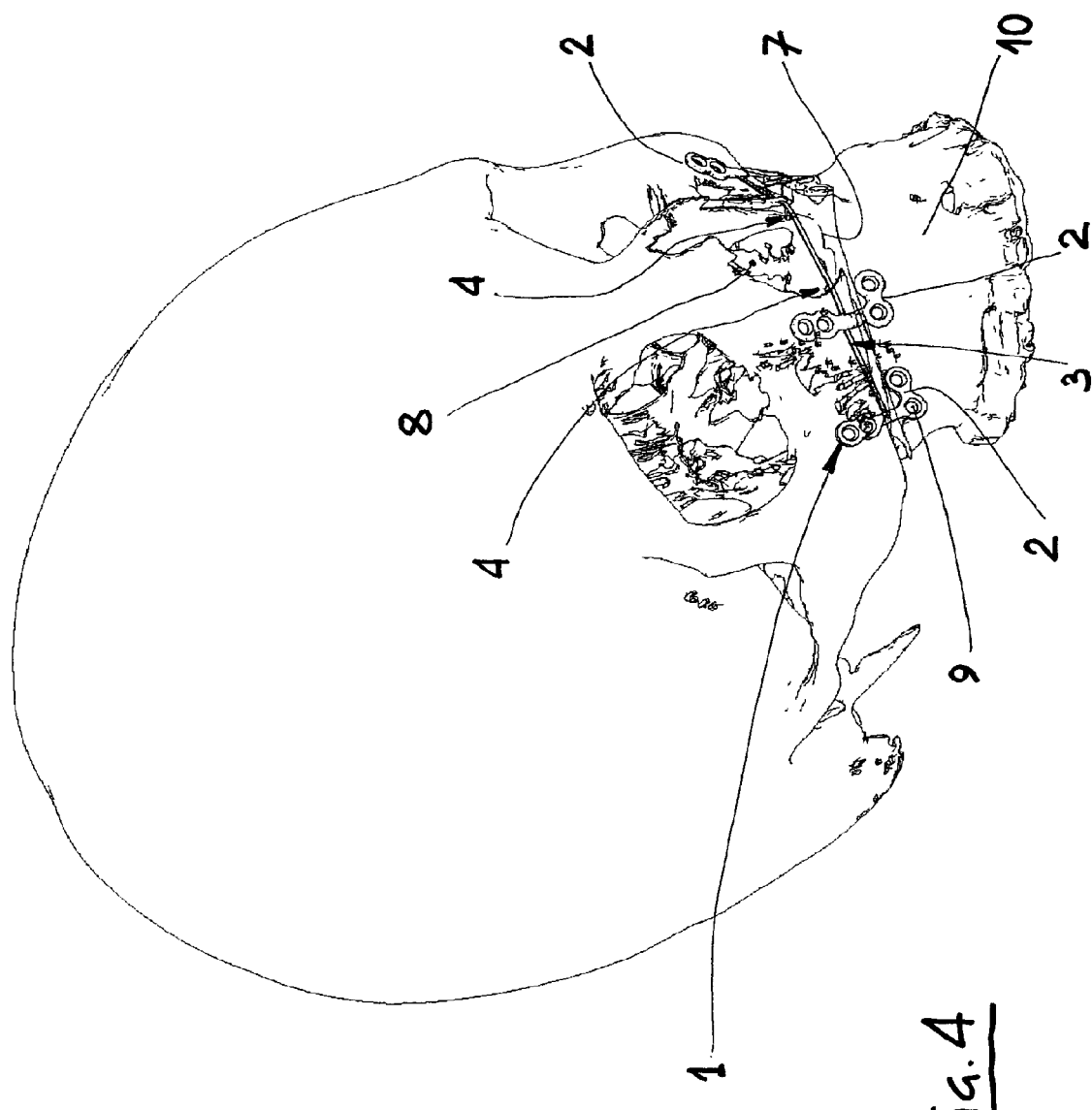
FIG. 4 illustrates a profile view of the same placing, in an ideal position, of the customized assembly of FIGS. 1 and 2 on the patient's upper jaw.

In the chosen embodiment, represented in FIGS. 1 to 4, the dental occlusion operation carried out relates exclusively to the upper jaw, also called maxillary.

As a variant embodiment, it is however clear that the invention will also apply to each repair of the lower jaw, also called mandible, whether this repair is carried out on its own or concomitantly with that of the upper jaw.

In this variant embodiment, it is only the shape of the connecting rod and the shapes of the osteosynthesis plates that will be modified, the latter being most often, for repairing the maxillary, of L-shaped and/or cross-shaped and/or crow's-foot-shaped.

In fact, in order to repair the mandible, osteosynthesis plates in I-shape, i.e. straight plates, are generally preferred.

Knowing the future anatomy of the patient on the basis of the data from a scanner of an MRI, as preliminary to the intended operation, an assembly 1 is made consisting of at least two osteosynthesis plates, four L-shaped ones in the example represented in FIGS. 1 to 4, which is formed: [0029] of the osteosynthesis plates 2 as such, which according precisely to the future anatomy of the patient and thus of the positions they will have to occupy on the jaw that is to be repaired, are each set in the appropriate shape, i.e. in customized fashion, with here and there the curvatures that will guarantee that they will perfectly follow the future anatomy desired, [0030] a rod 3 that connects together all the plates 2, said rod comprising furthermore two protrusions 4 corresponding very precisely to the two ends 5 and 6 of the base 7 of the nasal orifice 8 of the patient.

Each osteosynthesis plate 2 is, in known fashion, bored with several through holes 9, here four holes for each L-shaped plate, said holes being designed to accommodate the screws that, after the assembly 1 (also called assembly structure) is perfectly placed on the maxillary 10 of the patient, will ensure that the assembly will be fastened on said maxillary by being screwed by the surgeon into the bone parts that, disjoined after the operation, must be reunited by being placed one against the other.

The two protrusions 4 are for example advantageously made in the shape of studs or of fingers or of lugs or of spurs that protrude from the rod 3 in the direction of the patient's nasal orifice 8. Again, by virtue of its construction, the positions on the rod and the shapes of these protrusions 4 have been determined from the data known from the scanners or MRI.

Preferably, the rod 3 itself also follows perfectly the anatomy of the patient's maxillary bone or, as the case may be, that of the patient's mandibular bone; its curved and rectilinear parts are thus known from the aforementioned data and they will be reproduced identically on the rod when the assembly structure is constructed.

After having performed the desired operation, the surgeon places one against the other the disjoined bone parts, then the structure 1 is implanted by placing the two protrusions 4 in the lower corners 5 and 6 of the patient's nasal orifice 8, i.e. by lodging them at the two ends of the base 7 of said nasal orifice.

The structure 1 ideally occupies its place, determined in advance, in relation to the patient's maxillary and the surgeon then only needs to proceed with fastening said structure onto the maxillary by means of screws going through the holes 9 of the L-shaped osteosynthesis plates 2.

As the disjoined bone parts are thus fixedly reunited and need to remain so until the bone knits, the surgeon only has to eliminate from the structure 1 all its parts that have become useless, i.e. the connecting parts between the different osteosynthesis plates 2, only said plates thus remaining in the patient's mouth at the end of the operation.

To this effect, the surgeon cuts the rod 3 in the immediate vicinity of each of the plates 2, including that part of the rod that comprises the two protrusions 4.

In order to make easier this task of cutting the rod to eliminate it, the construction provides that said rod has, in the vicinity of each of the different plates 2 of the zones of reduced resistance illustrated by the mixed lines 11, the latter, for greater clarity of the figures having been schematized only at certain occasions.

The customized assembly 1 according to the invention— i.e. the osteosynthesis plates 2 and the rod 3—will advantageously be made of titanium, a biocompatible material nowadays commonly used in surgery, and said assembly is preferably made of a single piece.

It goes without saying that the invention is not limited only to the technical specifications given here above by way of example; on the contrary, it encompasses all possible embodiment variants, in particular that where another structure 1 is constructed that is adapted specifically for repairing a mandible, another structure wherein on the one hand the rod 3, instead of being more or less rectilinear, will have more the shape of an omega and, on the other hand, the I-shaped plates 2 will traditionally be substituted for the L-shaped plates chosen in the present example, but they could just as well be cross-shaped and/or shaped in crow's-foot.

What is claimed is:

1. An assembly for maxillary osteosynthesis of a jaw comprising:
   at least two osteosynthesis plates, each osteosynthesis plate comprising a first portion configured to be fixed to an upper bone part of a maxilla and a second portion configured to be fixed to a lower bone part of the maxilla, wherein the second portion of each osteosynthesis plate is immovably coupled to and offset from the respective first portion by a substantially orthogonal transition portion along an occlusal plane so as to modify an occlusional relationship between the maxilla and a mandible, the first portion and the second portion being configured to be located at opposing sides of at least one bone cut when the osteosynthesis plates are fixed to the maxilla, wherein each osteosynthesis plate has a pre-configured curvature in three dimensions based on a position that the plate will occupy when fixed to the upper and lower bone parts of the maxilla, the curvature being customized based on a future desired anatomy of the maxilla; and a connecting part connecting the osteosynthesis plates, the connecting part having a pre-configured shape defining at least two positions that the osteosynthesis plates will respectively occupy when fixed to the upper and lower bone parts of the maxilla, the shape being customized based on an anatomy of the maxilla.

2. The assembly of claim 1, wherein each of the first and second portions of each osteosynthesis plate comprises at least one aperture for fixing the portion to a respective bone part.

3. The assembly of claim 1, wherein the connecting part comprises a reference portion for orientating the assembly with respect to at least one of the upper and lower bone parts.

4. The assembly of claim 1, wherein the shape of the connecting part comprises a configuration of one or more of curved and rectilinear parts.

5. The assembly of claim 1, wherein the connecting part comprises zones of reduced resistance for use in removing the connecting part.

6. An assembly for maxillary osteosynthesis comprising:
at least two osteosynthesis plates,
each osteosynthesis plate having a pre-configured curvature which is customized based on a future desired anatomy of a patient's maxilla; and
a connecting part connecting the osteosynthesis plates, the connecting part having a pre-configured shape defining at least two positions that the osteosynthesis plates will respectively occupy when fixed to one or more bone parts, the shape being customized based on an anatomy of the patient's maxilla,
wherein the connecting part is coupled to each osteosynthesis plate between a first portion and a second portion of each osteosynthesis plate,
the first portion and the second portion being configured to be located opposing sides of at least one bone cut when the osteosynthesis plates are fixed to the maxilla,
wherein the first portion is configured to be fixed to an upper bone part of the maxilla and the second portion is configured to be fixed to a lower bone part of the maxilla,
wherein the second portion of each osteosynthesis plate is immovably coupled to and offset from the respective first portion by a substantially orthogonal transition portion along an occlusal plane so as to modify an occlusional relationship between the maxilla and a mandible, and wherein the connecting part comprises zones of reduced resistance for use in removing the connecting part.

7. A method of manufacturing an assembly for maxillary osteosynthesis comprising:
accessing data indicative of a future desired anatomy of a patient's maxilla; and
manufacturing an assembly for osteosynthesis comprising at least two osteosynthesis plates and a connecting part, each osteosynthesis plate comprising a first portion configured to be fixed to an upper bone part of the maxilla and a second portion configured to be fixed to a lower bone part of the maxilla, wherein the second portion of each osteosynthesis plate is immovably coupled to and offset from the respective first portion by a substantially orthogonal transition portion along an occlusal plane so as to modify an occlusional relationship between the maxilla and a mandible, the first portion and the second portion being configured to be located at opposing sides of at least one bone cut when the osteosynthesis plates are fixed to the maxilla,
wherein the manufacturing comprises:
defining a curvature of each osteosynthesis plate in three dimensions based on a position that the plate will occupy when fixed to the upper and lower bone parts of the maxilla, the curvature being customized on the basis of the accessed data, and
defining a connecting part for connecting together the osteosynthesis plates, the connecting part having a shape defining at least two positions that the osteosynthesis plates will respectively occupy when fixed to the upper and lower bone parts of the maxilla, the shape being customized on the basis of the accessed data, and
manufacturing the assembly such that the osteosynthesis plates exhibit the shape.

8. The method of claim 7, wherein each of the first and second portions of each osteosynthesis plate comprises at least one aperture for fixing the portion to a respective bone part.

9. The method of claim 7, wherein the connecting part comprises a reference portion for orientating the assembly with respect to at least one of the upper and lower bone parts.

10. The method of claim 7, wherein the shape of the connecting part comprises a configuration of one or more of curved and rectilinear parts.

11. The method of claim 7, wherein the connecting part comprises zones of reduced resistance for use in removing the connecting part.

12. The method of claim 7, wherein the data indicative of a future desired anatomy of a patient's maxilla is generated based on data from a scanner or magnetic resonance imaging (MRI).

13. The method of claim 7, wherein the data indicative of a future desired anatomy of a patient's maxilla is generated based on data from a simulated operation on the patient.

14. The method of claim 7, further comprising determining one or more reference portion positions based on data from a scanner or magnetic resonance imaging (MRI).

* * * * *